| (12) | United States Patent | (10) Patent No.: | US 8,998,871 B2 |
|---|---|---|---|
| | Kuroda et al. | (45) Date of Patent: | Apr. 7, 2015 |

(54) ABSORBENT ARTICLE WITH COMPRESSED CHANNEL PORTIONS

(75) Inventors: Kenichiro Kuroda, Kagawa (JP); Yuki Noda, Kagawa (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 696 days.

(21) Appl. No.: 11/942,831

(22) Filed: Nov. 20, 2007

(65) Prior Publication Data

US 2008/0119810 A1 May 22, 2008

(30) Foreign Application Priority Data

Nov. 22, 2006 (JP) ................... 2006-316346
Nov. 22, 2006 (JP) ................... 2006-316347

(51) Int. Cl.
*A61F 13/533* (2006.01)
*A61F 13/475* (2006.01)
*A61F 13/15* (2006.01)
*A61F 13/47* (2006.01)

(52) U.S. Cl.
CPC ............ *A61F 13/4756* (2013.01); *A61F 13/533* (2013.01); *A61F 13/15707* (2013.01); *A61F 13/4704* (2013.01)

(58) Field of Classification Search
USPC ............... 604/380, 385.101, 385.12, 385.201
See application file for complete search history.

(56) References Cited

U.S. PATENT DOCUMENTS

| 2,118,169 | A | * | 5/1938 | Crouse ........................... 604/380 |
|---|---|---|---|---|
| 2,788,003 | A | * | 4/1957 | Morin ............................ 604/366 |
| 2,896,618 | A | * | 7/1959 | Schaefer ........................ 602/47 |
| 2,952,260 | A | * | 9/1960 | Burgeni ......................... 604/374 |
| 3,442,268 | A | * | 5/1969 | Bird ............................... 604/380 |
| 3,653,382 | A | * | 4/1972 | Easley et al. ................... 604/370 |
| 3,848,599 | A | * | 11/1974 | Schaar ...................... 604/385.23 |
| 4,758,240 | A | * | 7/1988 | Glassman ..................... 604/379 |
| 5,173,351 | A | * | 12/1992 | Ruppel et al. ................. 428/174 |

(Continued)

FOREIGN PATENT DOCUMENTS

| CN | 1805721 | 7/2006 |
|---|---|---|
| JP | 60-69116 | 5/1985 |

(Continued)

OTHER PUBLICATIONS

Search Report dated Oct. 16, 2013, directed to EP Application No. 07832400.1; 3 pages.

(Continued)

*Primary Examiner* — Melanie Hand
*Assistant Examiner* — Paula L Craig
(74) *Attorney, Agent, or Firm* — Morrison & Foerster LLP

(57) ABSTRACT

An absorbent article is provided that improves adhesion to the skin and reduces leaks of bodily fluids by ensuring stable deformation thereof. The absorbent article has a liquid-permeable top sheet disposed on body-facing side of the absorbent article; a liquid-impermeable back sheet disposed on a clothing-facing side of the absorbent article; and a liquid-retainable absorbent body disposed between the top sheet and the back sheet. The absorbent body has a compressed channel formed into a concave shape in the body-facing side; and a space formed into a convex shape in the clothing-facing side toward the body-facing. The space is formed on both sides or on one side of a channel backside located on an opposing side of the compressed channel portion in the clothing-facing side.

8 Claims, 19 Drawing Sheets

(56) References Cited

U.S. PATENT DOCUMENTS

| | | | |
|---|---|---|---|
| 5,713,883 A * | 2/1998 | Hsieh | 604/385.01 |
| 5,840,404 A * | 11/1998 | Graff | 428/154 |
| 5,865,824 A * | 2/1999 | Chen et al. | 604/378 |
| 5,913,765 A * | 6/1999 | Burgess et al. | 493/403 |
| 5,925,439 A * | 7/1999 | Haubach | 428/178 |
| 5,964,743 A * | 10/1999 | Abuto et al. | 604/385.01 |
| 6,068,620 A * | 5/2000 | Chmielewski | 604/378 |
| 6,090,994 A * | 7/2000 | Chen | 604/378 |
| 6,149,638 A * | 11/2000 | Vogt et al. | 604/385.01 |
| 6,210,385 B1 | 4/2001 | Mizutani | |
| 6,492,574 B1 * | 12/2002 | Bednarz et al. | 604/378 |
| 6,500,159 B1 * | 12/2002 | Carvalho | 604/385.01 |
| 6,524,292 B1 * | 2/2003 | DiPalma et al. | 604/385.12 |
| 6,602,234 B2 * | 8/2003 | Klemp et al. | 604/385.01 |
| 6,617,490 B1 * | 9/2003 | Chen et al. | 604/380 |
| 6,642,432 B1 * | 11/2003 | Matsui et al. | 604/380 |
| 6,675,702 B1 * | 1/2004 | Maksimow | 100/41 |
| 7,122,713 B2 * | 10/2006 | Komatsu et al. | 604/380 |
| 7,303,808 B2 * | 12/2007 | Taneichi et al. | 428/198 |
| 7,678,442 B2 * | 3/2010 | Casey et al. | 428/156 |
| 7,754,940 B2 * | 7/2010 | Brisebois et al. | 604/380 |
| 2002/0165518 A1 * | 11/2002 | Datta et al. | 604/385.29 |
| 2003/0036741 A1 * | 2/2003 | Abba et al. | 604/385.101 |
| 2003/0125696 A1 * | 7/2003 | Morman et al. | 604/385.22 |
| 2004/0064113 A1 * | 4/2004 | Erdman | 604/361 |
| 2004/0127864 A1 * | 7/2004 | Sugito | 604/346 |
| 2004/0143233 A1 * | 7/2004 | Nakajima et al. | 604/385.101 |
| 2004/0243082 A1 | 12/2004 | Kinoshita et al. | |
| 2004/0253892 A1 * | 12/2004 | Baker et al. | 442/327 |
| 2004/0254552 A1 * | 12/2004 | Mangold | 604/367 |
| 2004/0254554 A1 * | 12/2004 | Mavinkurve et al. | 604/380 |
| 2004/0267220 A1 * | 12/2004 | Hull et al. | 604/380 |
| 2005/0124951 A1 * | 6/2005 | Kudo et al. | 604/380 |
| 2005/0148970 A1 * | 7/2005 | Kudo et al. | 604/378 |
| 2005/0182374 A1 * | 8/2005 | Zander et al. | 604/380 |
| 2006/0116653 A1 * | 6/2006 | Munakata et al. | 604/380 |
| 2006/0142724 A1 * | 6/2006 | Watanabe et al. | 604/385.04 |
| 2006/0276767 A1 * | 12/2006 | Ueminami et al. | 604/385.31 |
| 2006/0286353 A1 * | 12/2006 | Stridfeld et al. | 428/174 |
| 2011/0092944 A1 * | 4/2011 | Sagisaka et al. | 604/385.101 |
| 2011/0130737 A1 * | 6/2011 | Sagisaka et al. | 604/380 |
| 2013/0035656 A1 * | 2/2013 | Moriya et al. | 604/380 |

FOREIGN PATENT DOCUMENTS

| | | |
|---|---|---|
| JP | 09-108262 | 4/1997 |
| JP | 10-099372 | 4/1998 |
| JP | 11-299827 | 11/1999 |
| JP | 11-342154 | 12/1999 |
| JP | 2000-083992 | 3/2000 |
| JP | 2001-204759 | 7/2001 |
| JP | 2001-204760 | 7/2001 |
| JP | 2001-314445 | 11/2001 |
| JP | 2002-219144 A1 | 8/2002 |
| JP | 2003-024372 | 1/2003 |
| JP | 2004-181085 | 7/2004 |
| JP | 2006-20977 | 1/2006 |
| JP | 200668551 | 3/2006 |
| TW | 325995 | 2/1998 |
| TW | 329665 | 4/1998 |
| TW | 371626 | 10/1999 |

OTHER PUBLICATIONS

Notice of Reasons for Rejection mailed Jul. 3, 2012, directed to Japanese Application No. 2006-316347; 3 pages.

Office Action mailed Jun. 27, 2013, directed to TW Application No. 096144162; 7 pages.

Notice of Reasons for Rejection issued on Oct. 25, 2011, directed to Japanese Application No. 2006-316346; 2 pages.

Notice of Reasons for Rejection issued on Oct. 25, 2011, directed to Japanese Application No. 2006-316347; 2 pages.

* cited by examiner

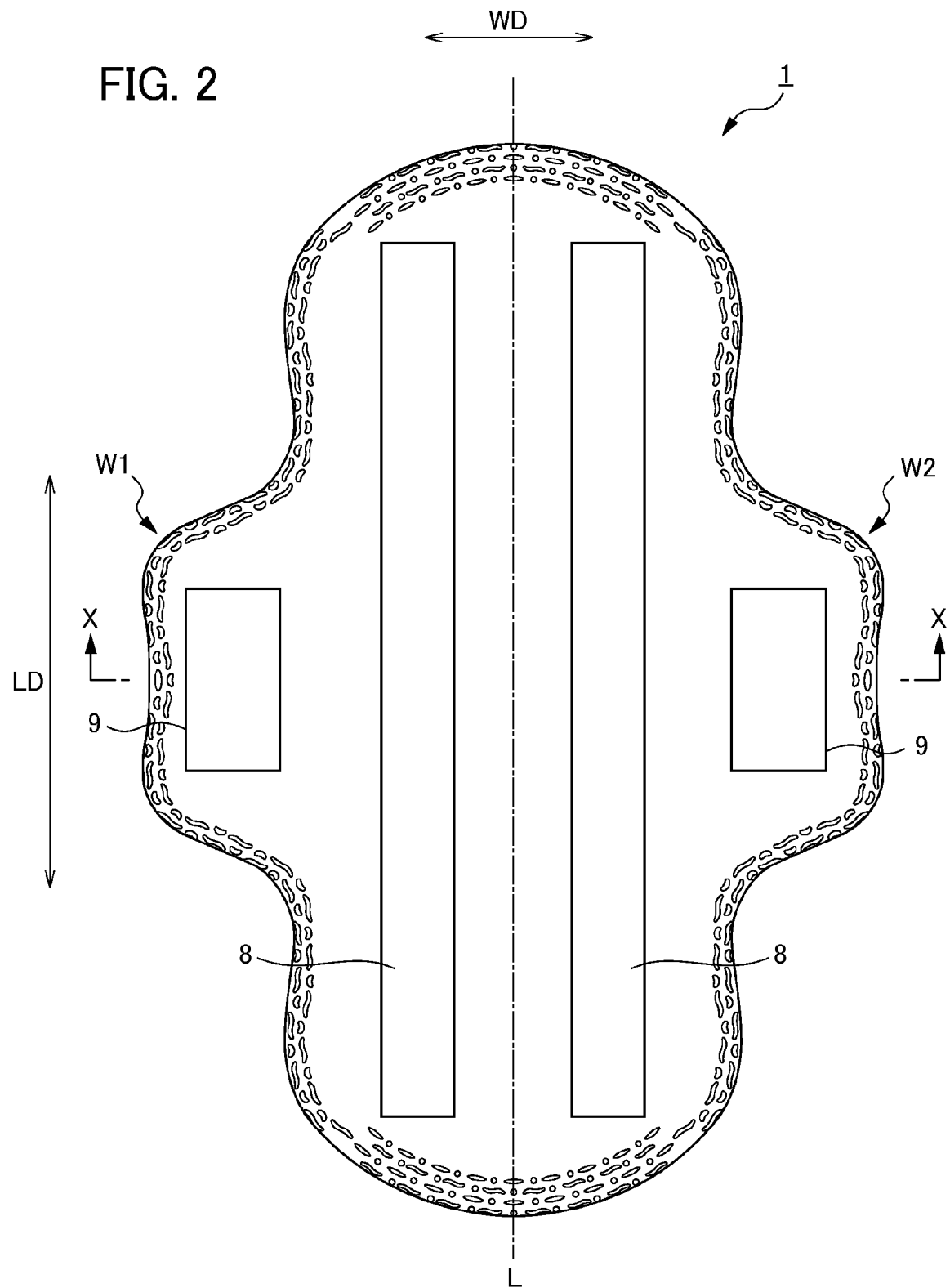

ABSORBENT ARTICLE WITH COMPRESSED CHANNEL PORTIONS

This application claims priority under 35 U.S.C. §119 from Japanese Pat. App. Nos. 2006-316346, and 2006-316347, filed on Nov. 22, 2006, which are incorporated herein by reference in their entireties.

FIELD OF THE INVENTION

The present invention relates to absorbent articles and manufacturing methods thereof. More particularly, the present invention relates to absorbent articles that have superior adhesion and leak-prevention properties, and manufacturing methods thereof.

BACKGROUND OF THE INVENTION

Conventionally, sanitary napkins, panty liners and urine-collecting pads, for example, are known as absorbent articles to absorb excreta such as menstrual blood and the like. Each of these absorbent articles has an absorbent body that absorbs and retains menstrual blood and the like; a liquid-permeable top sheet disposed on a surface on the absorbent article that contacts skin; and a liquid-impermeable back-sheet disposed on a surface of the absorbent article that contacts an undergarment. These napkins and the like are normally worn by being attached to underwear, for example.

However, for absorbent articles like the one described above, it is preferred that the absorbing portion of the absorbent body be placed in close contact to the area of excretion of the wearer to securely trap excreta that is discharged. The reason for this close contact is that if a gap is formed, for example, between the wearer's area of excretion and the absorbent article when the absorbent article is in use, the excreta can flow along the top sheet of the absorbent article and leak from the sides of the absorbent article and reach the buttocks of the wearer. This can soil the wearer's underwear and undergarments.

Particularly, in the case of a sanitary napkin worn by being attached to the wearer's underwear, it is easy for the underwear and area of excretion to become relatively displaced when the wearer's body moves. This displacing is a cause of side leaks of excreta. In addition, because a sanitary napkin, for example, is normally sandwiched between the wearer's underwear and femoral region, the napkin receives compressing force in a horizontal direct from the wearer's femoral region causing it to be compressed and become deformed. The deformation of the absorbent body causes a gap to form between the wearer's area of excretion and the sanitary napkin, which results in the wearer's underwear or undergarments becoming soiled.

Therefore, a sanitary napkin as disclosed in Japanese Unexamined Patent Application Publication No. 09-108262, which is incorporated by reference herein in its entirety and hereinafter referred to as Patent Publication 1, prevents side leaks of excreta and the like caused by twisting of the absorbent body. That is accomplished by forming a pair of compressed channels by consecutively press-treating the top sheet and absorbent body, and equipping each compressed channel in a length direction of the sanitary napkin.

The sanitary napkin disclosed in Patent Publication 1 arranges a pair of compressed channels to sandwich a core portion disposed in substantially the center in the width direction of the sanitary napkin, for example. A comparatively high-density compression portion and low-density compression portion are consecutively arranged in these compressed channels, thereby forming channels on the surface side of the sanitary napkin that contacts the skin. This prevents twisting that extends to the peripheral portions, even if side compression force is applied from the buttocks of the wearer causing twisting in substantially the center of the absorbent body. Therefore, menstrual blood and the like flows out along this twisting and is prevented from leaking to the sides from the peripheral portions.

In addition, Japanese Unexamined Patent Application Publication No. 10-99372, which is incorporated by reference herein in its entirety and hereinafter referred to as Patent Publication 2, discloses an absorbent article that improves adhesion by the absorbent article deforming to the wearer's skin by equipping a first flexible shaft that is emboss-formed from a surface side that contacts the wearer's skin and bends to the surface side that contacts the wearer's skin; and a second flexible shaft that is emboss-formed from a surface side that contacts the wearer's clothing and bends to the surface side that contacts the wearer's clothing.

The absorbent article disclosed in Patent Publication 2 equips both the first and the second flexible shafts on the surface sides that contact the wearer's skin and clothing of the absorbent article. This makes it easy for the absorbent article to bend to the surface sides that contact the wearer's skin and clothing when compressing force is applied from the wearer's buttocks, thereby making it easier to deform to a desired shape.

However, the sanitary napkin disclosed in Patent Publication 1 disposes compressed channels from substantially the center in the core thickness direction to the backside surface of the core. Therefore, pressure transferred from the compressed channels to the core when compressing force is applied from the wearer's buttocks in the width direction, and the article spreads in various directions from the surface sides that contact the skin and clothing in the thickness direction of the absorbent article. This causes the core to bend in various directions, which causes the problem of not being able to always attain a stable deformation.

Furthermore, the first flexible shaft of the absorbent article disclosed in Patent Publication 2 is formed in the thickness direction at the surface side that contacts the wearer's skin more than the surface side that contacts the wearer's clothing, so force transferred from the first flexible shaft when a compression force is applied in the width direction from the wearer's buttocks, and the absorbent article spreads in various directions in the thickness direction such to as surface sides that contact the wearer's skin or clothing. In addition, channels are formed on the surface side of the second flexible shaft that contacts the wearer's skin so there is the problem in that a stable deformation to that surface side is not possible because of the force of the second flexible shaft acting more in the direction of the clothing on the surface side that contacts the wearer's clothing.

SUMMARY OF THE INVENTION

The present invention solves the aforementioned problems. An object of the present invention is to provide an absorbent article that improves adhesion to the skin and reduces leaks of bodily fluids by ensuring stable deformation of the absorbent article.

To attain the aforementioned object, the inventors provide predetermined compressed channels in an absorbent article and a predetermined space at both sides of a surface side of the compressed channels that contacts the wearer's clothing to enable effective deformation of the absorbent article to complete the invention. Specifically, the absorbent article described below is provided.

In a first aspect of the present invention, an absorbent article has at least a portion thereof provided with a liquid-permeable top sheet disposed on a side of the absorbent article that contacts a wearer's skin; a liquid-impermeable back sheet disposed on a side of the absorbent article that contacts the wearer's clothing; and a liquid-retainable absorbent body disposed between the top sheet and the back sheet. The absorbent body has compressed channels formed into concave shapes in the surface side that contacts the wearer's clothing at the side that contacts the wearer's skin by compressing from the side that contacts the wearer's skin to the side that contacts the wearer's clothing; and spaces formed into convex shapes in the side that contacts the wearer's skin at the side that contacts the wearer's clothing by compressing from the side that contacts the wearer's clothing to the side that contacts the wearer's skin. The spaces are formed on both sides or on one side of channel backsides that are on an opposite side of the compressed channels on the side that contacts the wearer's clothing.

In a second aspect of the absorbent article according to the first aspect of the present invention, the absorbent body has a central core portion in substantially the center portion thereof, and the spaces are formed in the central core portion side of at least the channel backside portions of both sides of the channel backsides.

In a third aspect of the absorbent article according to the first or the second aspect of the present invention, the channel backside portion is formed to project to the surface side that contacts the wearer's clothing.

In a fourth aspect of the absorbent article according to any one of the first to third aspects of the present invention, at least a portion of the top sheet is formed to extend in a width direction perpendicular to a length direction of the absorbent article.

In a fifth aspect of the absorbent article according to any one of the first to fourth aspects of the present invention, at least a portion of the surface side that contacts the wearer's skin in the absorbent body is formed to extend in the width direction of the absorbent article.

In a sixth aspect of the absorbent article according to any one of first to fifth aspects of the present invention, at least a portion of the channel backside portion is joined to the back sheet.

In a seventh aspect of the absorbent article according to any one of the first to sixth aspects of the present invention, adhesive portions are disposed at opposite sides of the channel backside portions at the surface side that contacts the wearer's clothing.

In an eighth aspect of the absorbent article according to any one of the first to seventh aspects of the present invention, the absorbent body is pushed upward by the channel backside portions fitting into the spaces.

According to a ninth aspect of the present invention, a manufacturing apparatus of the absorbent article according to any one of the first to eighth aspects of the present invention includes a compressed channel forming means that forms concavely shaped compressed channels in the surface side that contacts the wearer's clothing by compressing the absorbent body from the surface side that contacts the wearer's skin and the surface side that contacts the wearer's clothing, and convexly shaped spaces in the surface side that contacts the wearer's skin, in which the compressed channel forming means has an upper die roller having a convex portion formed in a predetermined pattern on a surface thereof; and a lower die roller formed on the surface with a concave portion that meshes with the convex portion, to manufacture an absorbent article that is formed with compressed channels and spaces by compressing the absorbent body using the upper die roller and the lower die roller with at least the absorbent body in a clamped state.

According to a tenth aspect of the present invention, a manufacturing method of the absorbent article according to any one of the first to eighth aspects of the present invention includes a compressed channels forming process that forms concavely shaped compressed channels in a surface side that contacts the wearer's clothing by compressing the absorbent body from the surface side that contacts the wearer's skin and the surface side that contacts the wearer's clothing, and convexly shaped spaces in the surface side that contacts the wearer's skin, in which the compressed channels forming process has an upper die roller having a convex portion formed in a predetermined pattern on a surface thereof; and a lower die roller formed on the surface with a concave portion that meshes with the convex portion, to manufacture an absorbent article that is formed with compressed channels and spaces by compressing the absorbent body using the upper die roller and the lower die roller with at least the absorbent body in a clamped state.

Thus, the present invention provides an absorbent article that improves adhesion to the skin and reduces leaks of bodily fluids.

BRIEF DESCRIPTION OF THE DRAWINGS

The invention will become more readily apparent from the Detailed Description of the Invention, which proceeds with the reference to the drawings, in which:

FIG. 2 is a backside view of the sanitary napkin shown FIG. 1;

Figure 1:
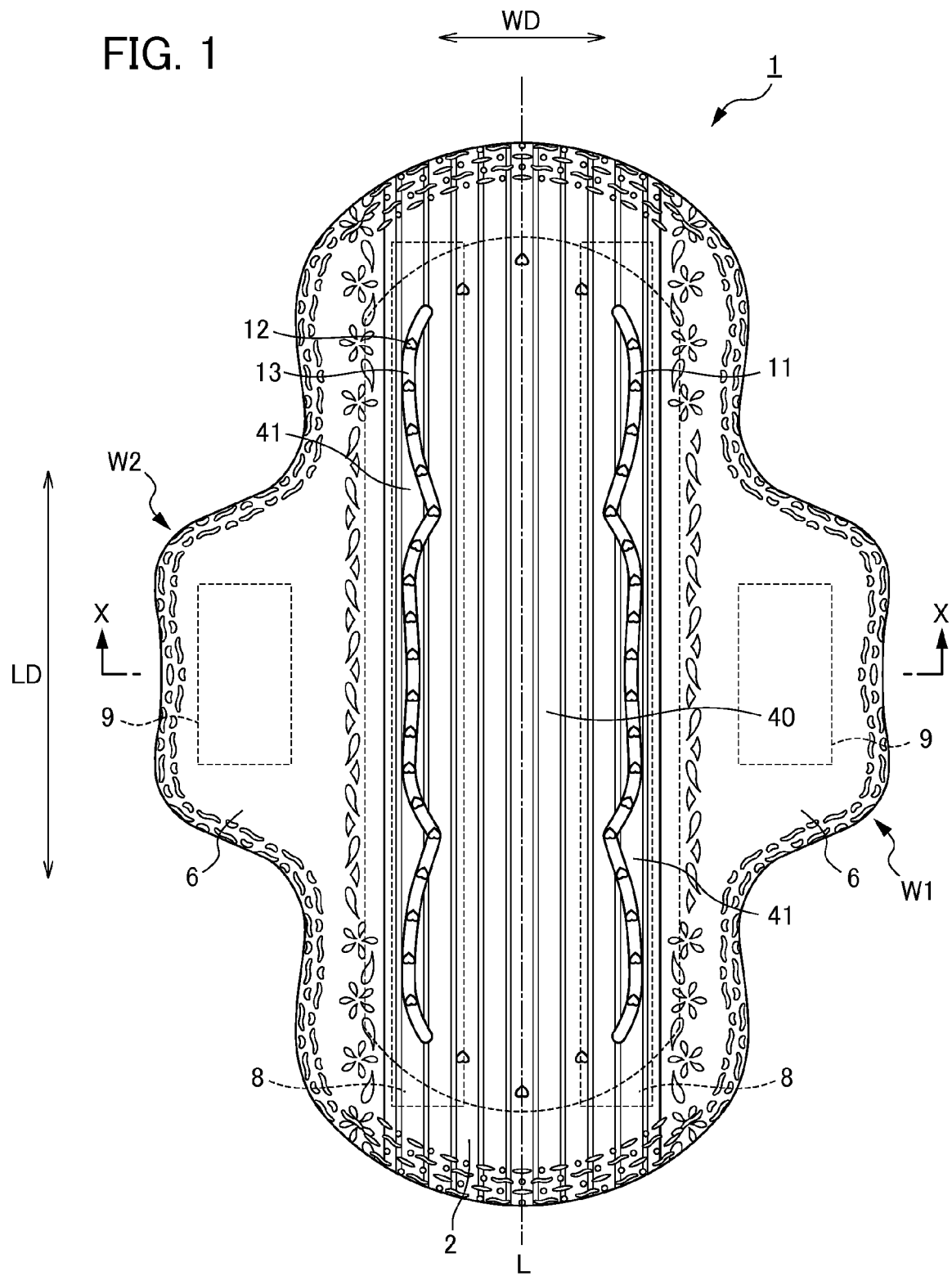
FIG. 1 is an elevation view of a sanitary napkin according to a first embodiment of the present invention.

In the figures, elements that are repeatedly illustrated are consistently identified by a single reference numeral.

DETAILED DESCRIPTION OF THE INVENTION

The following explains preferred embodiments of the present invention with reference to the drawings provided. It should be noted that the present invention is in no way limited to the embodiments below, nor is the technical range limited to the embodiments.

In addition, the absorbent article according to the present invention is worn at the crotch area of a human body with the object of absorbing menstrual blood, urine, and discharge from the womb or the like excreted from the human body; however, the embodiments below use an example of implementation to a sanitary napkin with the main object of absorbing menstrual blood excreted from the vaginal orifice of a female human being. Of the two surfaces of the absorbent article, one side is a surface that contacts the skin and faces the area of excretion. The other, opposite side, is a surface that contacts clothing, regardless of whether clothing is being worn on the outside.

1. First Embodiment
1-1. General Description

The following explains the overall structure of the absorbent article of the present invention using the sanitary napkin 1 of the first embodiment.

As shown in FIGS. 1 to 3B, the sanitary napkin 1, which is the absorbent article according to the first embodiment of the present invention, is equipped with a liquid-permeable top sheet 2 that composes a top surface layer, disposed on the surface that contacts the wearer's skin; a liquid-impermeable back sheet 3 that composes a back surface side layer, disposed on the surface that contacts the clothing of the wearer; and a liquid-retainable absorbent body 4 that composes the absorbent layer, and is enveloped in tissue 7. Adhesive portions 8 are established on the surface side of the back sheet 3 that contacts the wearer's clothing. The sanitary napkin 1 is affixed to the wearer's underwear or the like at these adhesive portions 8. Moreover, in the first embodiment, the sanitary napkin 1 is equipped with a liquid-permeable middle sheet 5 arranged between the top sheet 2 and absorbent body 4; a side sheet 6 that composes a portion of the top surface layer; and side flaps W1 and W2 that extend in the width direction (WD) of the sanitary napkin 1. The side flaps W1 and W2 also have adhesive portions 9.

Furthermore, the sanitary napkin 1 is provided with compressed channels 11 that are compressed channel portions formed into a concave shape from the surface side that contact a side of the top sheet 2 toward the back sheet 3. The sanitary napkin 1 is separated the absorbent body 4 into a core portion 40 and side portions 41 by these compressed channels 11. Projections 15, which are back side channels, are formed on the surface side that contacts the clothing of the compressed channels 11. Spaces 16, provided on both sides sandwiching the projections 15, are formed into convex shapes facing from the surface side that contacts the clothing toward the surface side that contacts the skin.

1-2. Top Sheet

The top sheet 2 is disposed on the wearer's body side when the sanitary napkin is in use and contacts the area of excretion. The entire surface or a portion of the top sheet member 2 can be liquid-permeable. In addition, that member can be composed of one sheet member, or it can be composed by adjoining a plurality of sheet members. In this embodiment, the top sheet 2 may be equipped with a liquid-permeable region substantially in the center portion in the width direction (WD) of the sanitary napkin 1, and the end sides in the width direction (WD) may be covered by a liquid-impermeable side sheet 6.

The middle sheet 5 allows excreta that have permeated the top sheet 2 to pass into the absorbent body 4, and functions as a cushion while the sanitary napkin is in use. The absorbent body 4 is enveloped in the tissue 7, and is equipped with a substantially oval core 40 substantially in the center of the width direction (WD) of the sanitary napkin 1. The core 40 is a region surrounded by the compressed channels 11. Sides 41 are formed on both sides of the core 40 in the width direction (WD). The core 40 and sides 41 are partitioned by the compressed channels 11. The back sheet 3 uses a liquid-impermeable sheet member to prevent excreta and the like retained in the absorbent body 4 from leaking to the surface side that contacts the clothing of the wearer.

1-3. Compressed Channels and Spaces

Figure 3A:
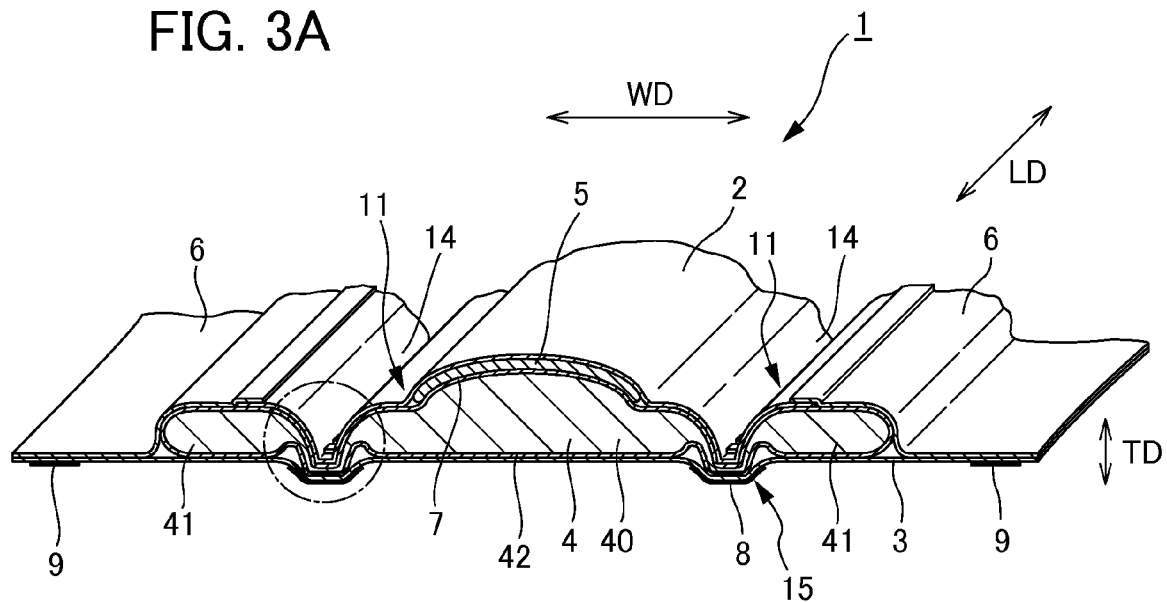
FIG. 3A is a sectional view of X-X of the sanitary napkin shown FIG. 1.
Figure 3B:
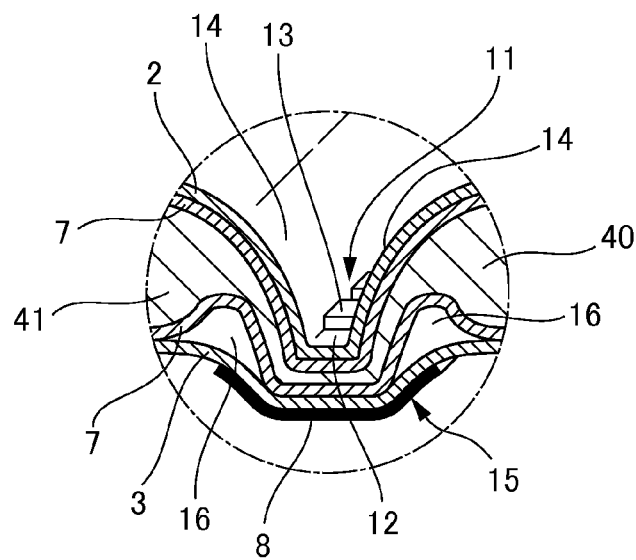
FIG. 3B is a partially enlarged view of the sanitary napkin shown FIG. 3A.
Figure 4:
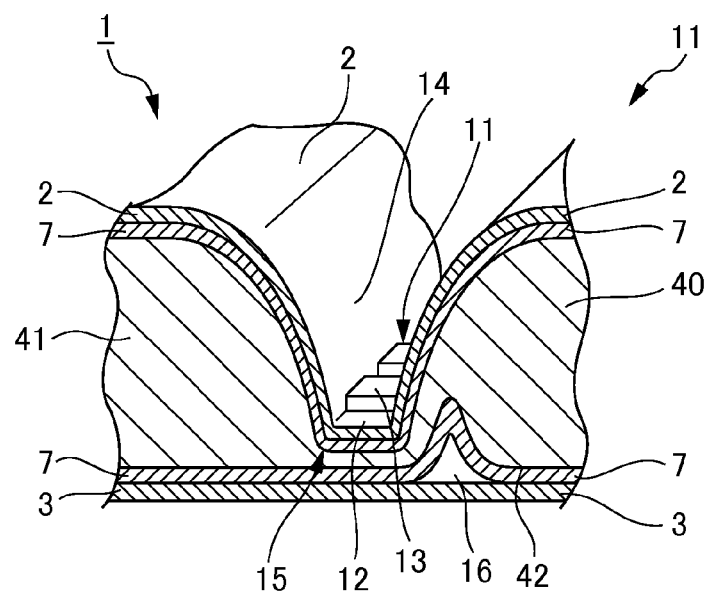
FIG. 4 is a partially enlarged view of another shape of the sanitary napkin according to a second embodiment.

The compressed channels 11 are disposed to extend in the length direction (LD) of the sanitary napkin 1 to sandwich the core 40. Specifically, as shown in FIGS. 3A and 3B, the compressed channels 11 are equipped with concave portions 12 formed by high compression, and convex portions 13 formed by low compression; these are formed by consecutively compressing with high and low pressures.

In addition, the compression channels 11 are equipped on the surface side that contacts the clothing with projections 15 that project more to the surface side that contacts the clothing than a back surface 42 that is the surface side of the core 40 that contacts the clothing of the wearer. Spaces 16, provided on both sides sandwiching the projections 15, are formed into concave shapes facing from the surface side that contacts the wearer's clothing toward the surface side that contacts the skin.

The spaces 16 in this embodiment are formed at both sides to sandwich the projections 15; on the surface side on the absorbent body 4 that contacts the wearer's clothing, they are formed to be convex shapes to face from the surface side that contacts the wearer's clothing toward the surface side that contacts the wearer's skin. The peaks of the spaces 16 are formed to be disposed 2 mm more than the backside surface 42 of the core 40 to the surface side that contacts the wearer's skin. In the other way, the differences in heights in the thickness direction (TD) of the absorbent body 4 between the concave portions 12 formed at the bottom of the compressed channels 11 and the peaks of the spaces 16 are formed to be 2 mm. Preferably, the differences in heights in the thickness direction (TD) of the absorbent body 4 between the concave portions 12 formed at the bottom of the compressed channels 11 and the peaks of the spaces 16 are in a range of 0.5 to 10 mm. If the differences in height in the thickness direction (TD) of the absorbent body 4 between the concave portions 12 and the spaces 16 are in a range of 0.5 to 10 mm, it is easier for the projections 15 to enter the spaces 16 formed on surface side of the core 40 that contacts the wearer's clothing.

It should be noted that in this embodiment, the spaces 16 are provided on both sides that sandwich projections 15, but it is acceptable to provide spaces on the core 40 side. Providing spaces 16 at the core 40 side makes it possible for the projections 15 to bend to the spaces 16 side. In the other way, it is possible for the projections 15 to incline toward the center of the width direction (WD) of the sanitary napkin 1 via the spaces 16. This makes it possible to ensure stable deformations of the projections 15 and the core 40 and to improve adherence to the skin.

The compressed channels 11 are provided with a pair of walls 14 formed by engagement by the embossing apparatus described below. The walls 14 are formed, for example, when the top sheet 2 and absorbent body 4 are pressed in the thickness direction (TD) of the sanitary napkin 1, and there is high tensile stress generated in substantially the center of the thickness direction (TD) of the sanitary napkin 1 which elongates the absorbent body 4. The walls 14 with the absorbent body 4 stretched are formed to a low density in substantially the center. This low-density portion suppresses the spreading of excreta transferred from the high-density portion, when the core 40 absorbs excreta.

Figure 5:
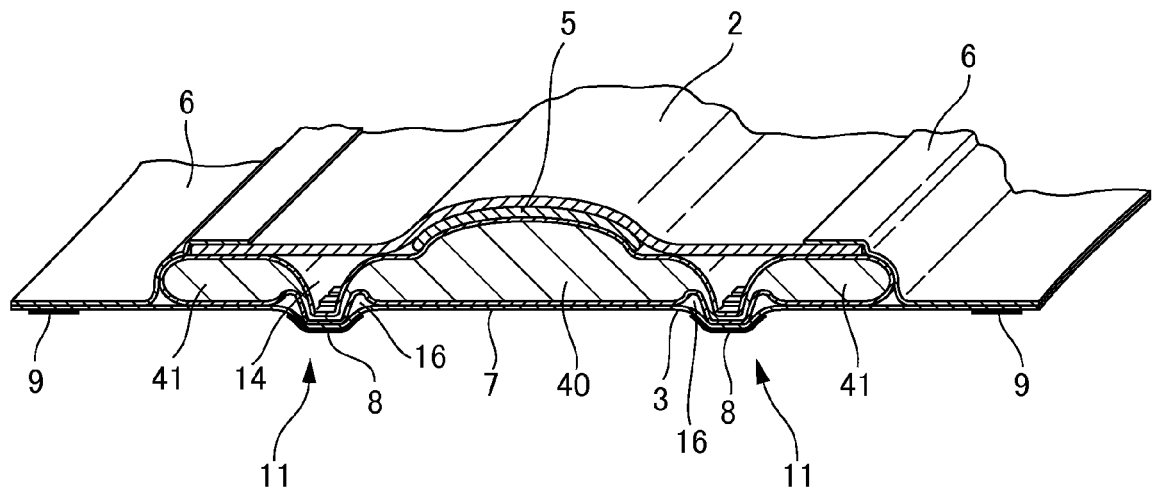
FIG. 5 is a sectional view of another shape of the sanitary napkin according to the first embodiment.

The compressed channels 11 are formed by consecutively pressing the top sheet 2 and absorbent body 4 from the surface side that contacts the wearer's skin and the surface side that contacts the wearer's clothing, but there is no limitation thereto in the present invention. It is also acceptable to form the compressed channels 11 by consecutively compressing each of the surface side that contacts the wearer's skin and the surface side that contacts the wearer's clothing only on the absorbent body 4, for example, as shown in FIG. 5. If the compressed channels 11 are formed only in the absorbent body 4, the absorbent body 4 is easily deformed because the top sheet 2 does not apply compression to the absorbent body 4. It is also acceptable to form the compressed channels 11 by consecutively compressing each of the surface side that contacts the wearer's skin and the surface side that contacts the wearer's clothing for the middle sheet 5 and the absorbent body 4. For example, if the middle sheet 5 and the absorbent body 4, which is formed by a synthetic resin fiber or the like, are consecutively compressed from the surface side that contacts the wearer's skin and the surface side that contacts the wearer's clothing, it is easy to retain the projected shape of the compressed channels 11 on the surface side that contacts the wearer's clothing.

It is acceptable that the compressed channels 11 are provided with openings in the concave portions 12. By providing these openings, it is possible for the excreta transferred from the top sheet 2 to fall into the back sheet 3 provided on the surface side of the core 40 that contacts the wearer's clothing, which is underwear. By allowing excreta to fall into the back sheet 3, it is possible to suppress the spreading of excreta to the surface layer that includes the top sheet 2. Also, it is acceptable to equip openings in the side walls 14. In such cases, in the same way, it is possible for the excreta transferred from the top sheet 2 to fall into the back sheet 3 provided on the surface side of the core 40 that contacts the wearer's clothing, which is underwear. It should be noted that the openings are preferred to be a size that does not partition the side walls.

In addition, in this embodiment, adhesive portions 8 are provided at all positions that correspond to the projections 15 on the backside surface of the compressed channels 11. However, this is not to be construed as a limitation in the present invention. It is acceptable to provide the adhesive portions 8 at positions that correspond to at least a part of the projections 15.

In this embodiment, adhesive portions 8 for slip prevention are disposed on the surface side that contacts the wearer's clothing of the compressed channels 11 on the back sheet 3 so as not to obstruct convex deformation of the core 40 to the surface side that contacts the wearer's skin, but the present invention is not limited thereto. It is acceptable to provide the adhesive portions 8 in a state that includes the center in the length direction (LD) of the sanitary napkin 1, on the surface side of the back sheet 3 that contacts the wearer's clothing. It is possible to dispose projections 15 on the surface side that constantly contacts the wearer's clothing more than the core 40 using hot-melt that bonds the absorbent body 4 and back sheet 3, and to enable the core 40 to convexly deform to the underwear 70 joined to the core 40.

In addition, it is acceptable that the backside surface 42 of the core 40 is detachably bonded to the back sheet 3 with the hot-melt of the absorbent body 4 and back sheet 3. Specifically, it is acceptable that at least the back surface of the compressed channels 11 and back sheet 3 are bonded. This makes it possible for the back sheet 3 and the backside surface 42 of the core 40 to separate and form a predetermined space when a compressing force is applied from the buttocks of the wearer in the width direction (WD). The projections 15 slip into the space, thereby enabling a stable deformation of the core 40.

Figure 6A:
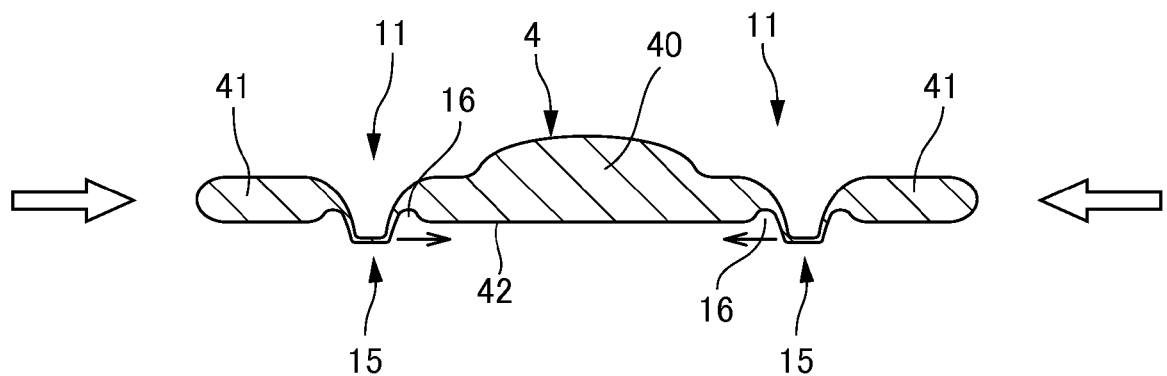
FIG. 6A is a schematic view illustrating a deformed state of the sanitary napkin according to the first embodiment.
Figure 6B:
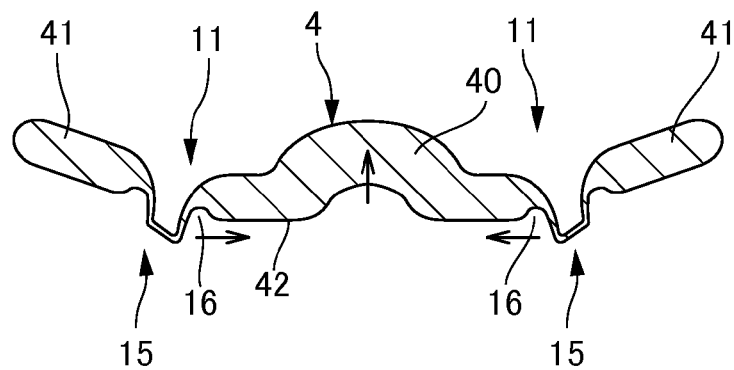
FIG. 6B is a schematic view illustrating a deformed state of the sanitary napkin according to the first embodiment.

In this way, the sanitary napkin 1 is equipped with the compressed channels 11 and spaces 16 so it is possible for the core 40 to convexly deform in a stable manner to the surface side that contacts the wearer's skin. For example, when a compressing force is applied by the wearer from the buttocks, a compressing force is added in the directions of the arrows in FIG. 6A. At that time, the compressing force is transferred to the core 40 via the compressed channels 11. Then, as shown in FIG. 6B, because spaces 16 are provided on both sides the projections 15 move to be deformed towards the backside surface 42 side of the core 40. Specifically, the projections 15 move to slip into the spaces 16 formed between the backside surface 42 of the core 40 that is adjacent to the projections 15. The projections 15 that move and slip into the spaces transfer the compressing force to further raise the core 40 from the backside surface 42 of the core 40. This causes the core 40 to deform and project to the surface side that contacts the wearer's skin, allowing close adherence to the area of excretion of the wearer.

Figure 7A:
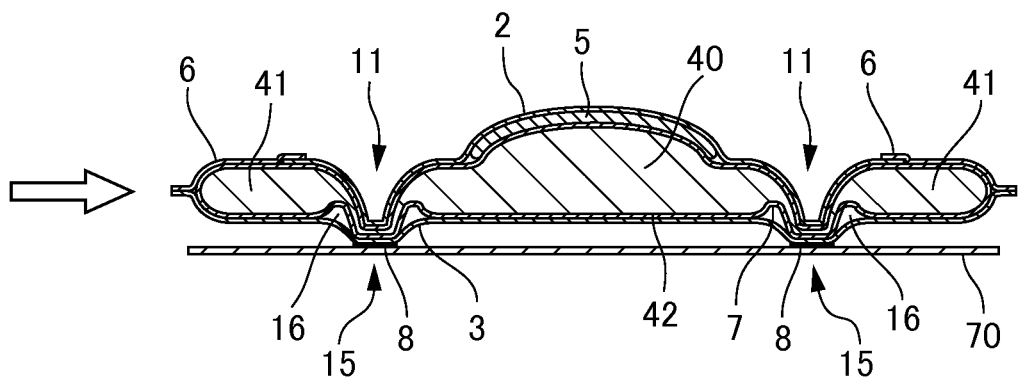
FIG. 7A is a sectional view showing a relationship of the compressed channels and slip-stoppers of the sanitary napkin according to the first embodiment.
Figure 7B:
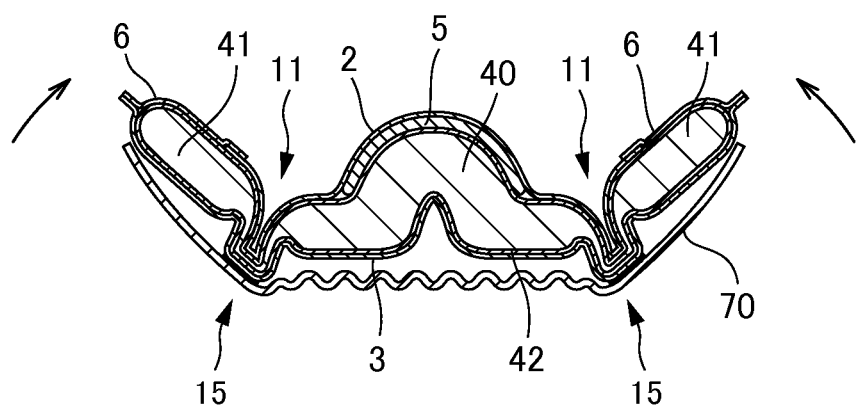
FIG. 7B is a sectional view showing a relationship of the compressed channels and slip-stoppers of the sanitary napkin according to the first embodiment.

In addition, the sanitary napkin 1, as shown in FIGS. 7A and 7B, is fastened to the underwear 70 at the surface side of the compressed channels 11 that contacts the wearer's clothing, in other words at the projections 15. This makes it possible to position the compressed channels 11 on the surface side that contacts the wearer's clothing more than the core 40 so it is possible for the core 40 to convexly deform in a stable manner.

Furthermore, the sanitary napkin 1 is attached by the side flaps W1 and W2 folding over to the surface side that contacts the wearer's clothing of the underwear 70 so that when a compressing force is applied from the wearer's buttocks in the width direction (WD), for example, action in the thickness direction (TD) of the sides 41 is restricted, thereby making it easier for the projections 15 to slip into the spaces 16, and enabling the sanitary napkin 1 to deform in a stable manner.

2. Other Embodiments

Other embodiments are explained with reference to FIGS. 8 to 13. Portions of the following embodiments that are not described are the same as the first embodiment. Furthermore, when the numbers that are used in the drawings are the same as the first embodiment, the same numbers are applied.

2-1. Second Embodiment

Figure 8:
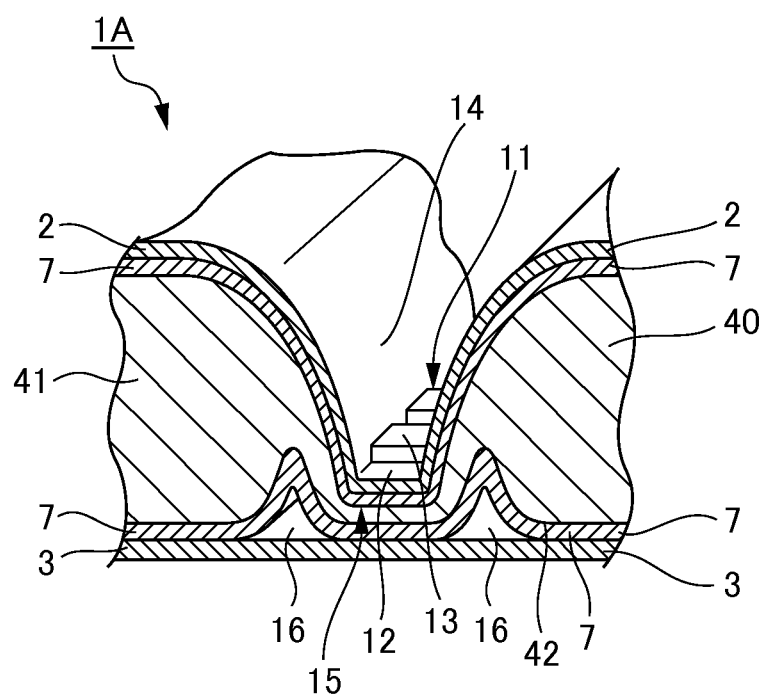
FIG. 8 is a partially enlarged view of a sanitary napkin according to the second embodiment of the present invention.
Figure 9:
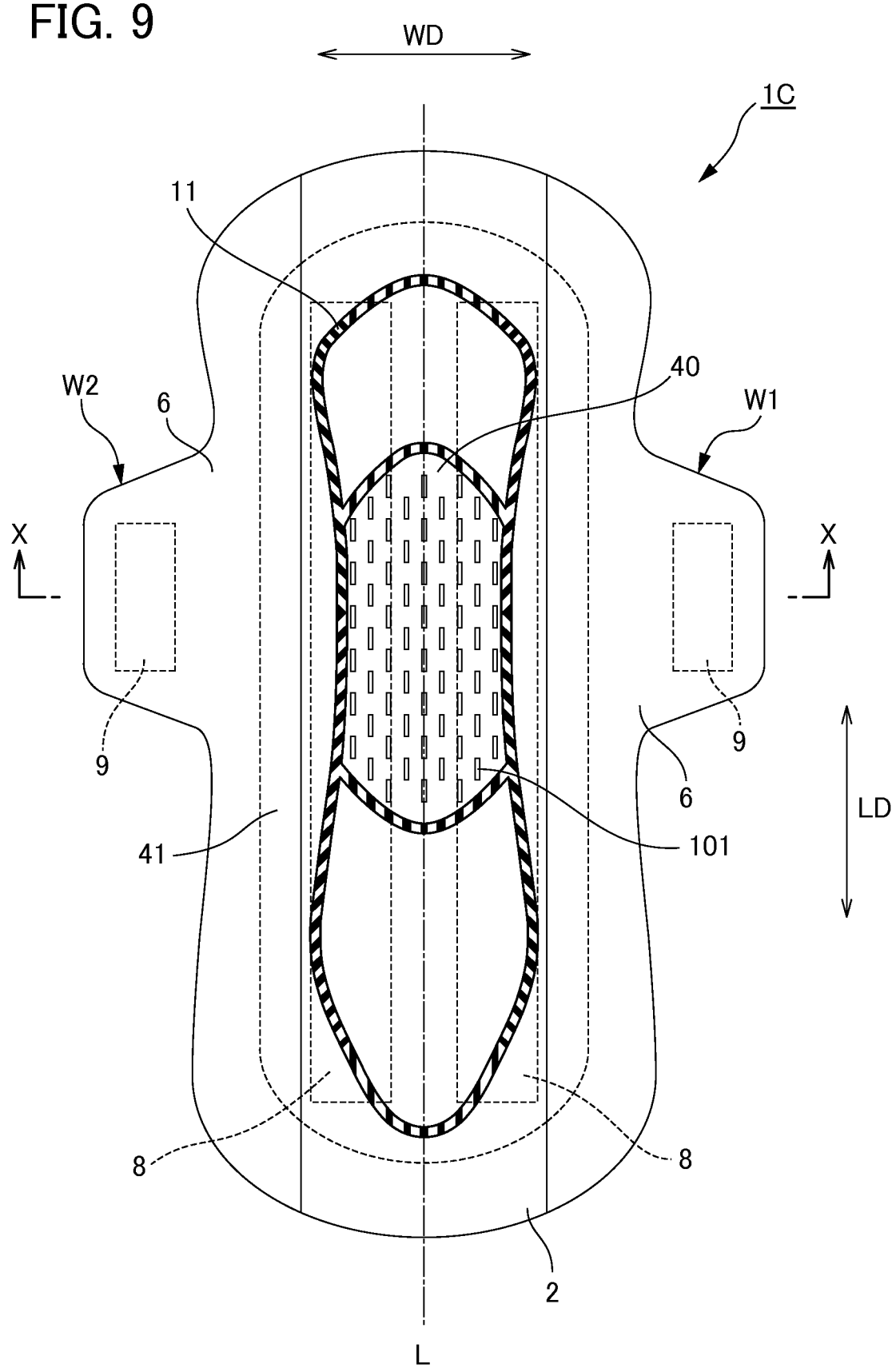
FIG. 9 is a plan view of a sanitary napkin according to a third embodiment of the present invention.
Figure 10A:
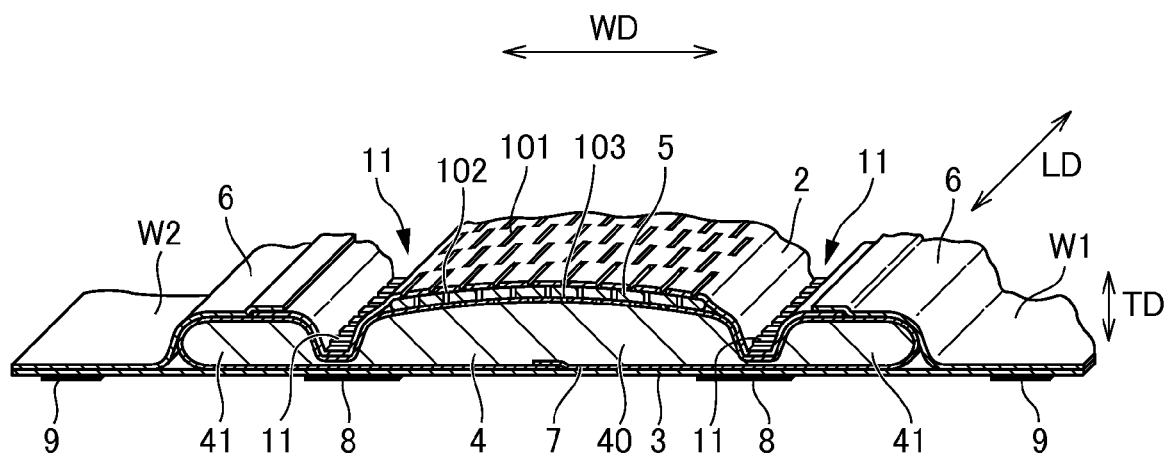
FIG. 10A is a sectional view illustrating a sanitary napkin according to the third embodiment of the present invention.
Figure 10B:
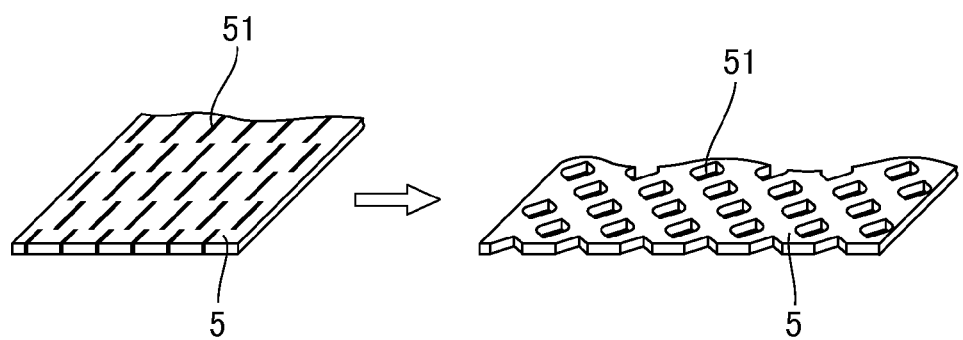
FIG. 10B is a partially enlarged view of a middle sheet of the sanitary napkin according to the third embodiment.

A second embodiment of the sanitary napkin 1A is explained with reference to FIG. 8. A partially expanded view of the compressed channels 11 of the sanitary napkin 1A is shown in FIG. 8 to facilitate explanation of the feature of the present invention. As shown in FIG. 8, the concave portions 12 of the compressed channels 11 in the sanitary napkin 1A according to the second embodiment are provided more on the surface side of the core 40 that contacts the wearer's skin than the backside surface 42. In this way, if the concave portions 12 of the compressed channels 11 are provided to be more on the surface side of the core 40 that contacts the wearer's skin than the backside surface 42, it is possible for the projections 15 to enter the spaces 16 when a compressing force is applied in the width direction (WD) from the wearer's femoral region, because spaces are formed on both sides of the compressed channels 11. This makes it possible to project the core 40 to the surface side that contacts the wearer's skin.

2-2. Third Embodiment

A third embodiment of the sanitary napkin 1C is explained with reference to FIGS. 9 to 13.

As shown in FIGS. 9 to 13, in the sanitary napkin 1C of the third embodiment, a plurality of holes 101, 102, and 103 formed substantially longitudinally are provided extending in the length direction (LD) of the sanitary napkin 1C for each of the top sheet 2, the middle sheet 5, and the tissue 7. The holes 101, 102, and 103 are formed to have a slit shape and to be along the compressed channels 11 in the core 40.

Figure 11:
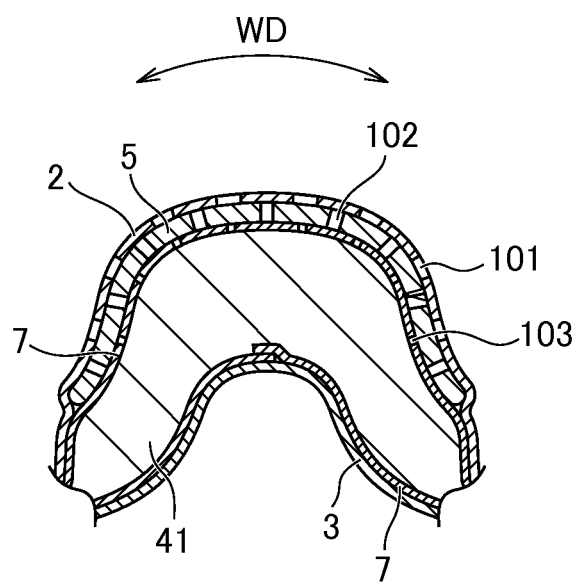
FIG. 11 is a view of opening holes in each layer of the sanitary napkin of the third embodiment when forming a convex-shaped core portion.

By providing the top sheet 2, middle sheet 5 and tissue 7 with the holes 101, 102, and 103, the top sheet 2, middle sheet 5 and tissue 7 are able to stretch in the width direction (WD) because the holes 101, 102, and 103 can be pulled in the width direction (WD) and deform into a substantially diamond shape (see FIG. 11) if the core is deformed to be a convex shaped. For example, if the core 40 is deformed into a convex shape by a compressing force generated from the wearer's buttocks, the holes 101, 102, and 103 widen forming holes, as shown in FIG. 11, so the convex deformation of the core 40 is not hindered. It should be noted that to form a convex shape without pushing in the core 40, it is acceptable for at least the sheet material disposed to be more on the surface side that contacts the wearer's skin than the absorbent body 4 to be elastic.

By providing the holes 101, 102, and 103 in each of the top sheet 2, middle sheet 5 and tissue 7, they can be extended or contracted and expanded in the width direction (WD) of the sanitary napkin 1. Therefore, the absorbent body 4 is not compressed even when the core 40 is deformed into a convex shape by a force conducted from the sides 41. This makes it possible to maintain a low density of the top sheet 2 and the like. For example, bodily fluids and the like will not return to the top sheet side even if pressure is applied by the movement of the wearer after deforming to a convex shape. In other words, it is possible to reduce discomfort caused by rewetting. Furthermore, it is possible to reduce the return of bodily fluids and the like from the absorbent body 4 when deforming to a convex shape because the top sheet 2 does not compress the absorbent body 4.

Figure 12:
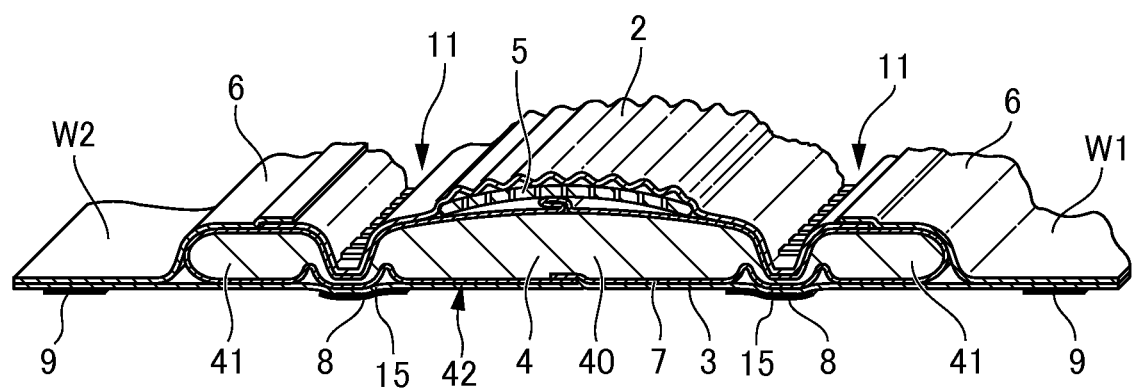
FIG. 12 is a view of another embodiment of the sanitary napkin according to the third embodiment.
Figure 13:
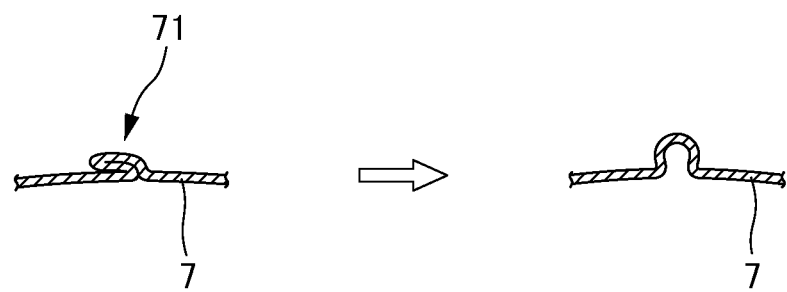
FIG. 13 is a partially enlarged view of a tissue of the sanitary napkin according to the third embodiment.

The sanitary napkin 1C can be formed into an uneven corrugated shape on the top sheet 2, as shown in FIG. 12. This ensures an amount of extension of the top sheet 2 in the width direction (WD), and enables the top sheet 2 to extend easily in the width direction (WD). Furthermore, the tissue 7 that envelops the absorbent body 4 can be provided with a folded portion 71. By providing the folded portion 71, an ability to extend is imparted if required when deforming convexly. This enables the absorbent body 4 to extend in the width direction (WD) the amount that it is allowed to extend. (See FIG. 13.)

In addition, it is acceptable to implement an elongating means as described above in all sheet members. If it is considered that the distance that the sheet member disposed on the outer surface side that contacts the wearer's skin extends is longer, it is preferably provided at least on the top surface layer of the surface side that contacts the wearer's skin. Furthermore, not only treatment of the sheets is acceptable, but it is also acceptable to use a sheet that implements coil-shaped crimped fibers, fibers that can stretch, such as urethane, or to reduce the fusing point of the sheet to make it easier to extend in the width direction (WD). It is also acceptable to strengthen the fiber orientation in the length direction (LD), thereby reducing their tensile strength in the width direction (WD) and applying extensibility, and implement extensibility in the width direction (WD) by providing openings. In addition, it is acceptable to form the sheets and to provide a predetermined space between the top sheet 2 and the absorbent body 4 without the sheet itself being able to stretch. This makes it possible to easily bias deformation in the same way as above because a deformation space is formed for the absorbent body 4 and the like to deform.

Each of the top sheet 2, the middle sheet 5, and the tissue 7 is preferred to be bonded by a spiral-shaped hot-melt adhesive so as not to hinder extending thereof in the width direction. Also, it is acceptable, for example, to bond these using a spray coating or the like, or a spiral-shaped hot-melt adhesive extending in the length direction. Furthermore, it is also acceptable to join each of the top sheet 2, the middle sheet 5, and the tissue 7 by embossing between the holes 101 with a predetermined emboss 114, for example. In such a case, for the shape of the emboss 114, it is acceptable to join the sheets by forming polygons, ovals, long shapes, and star shapes, in addition to the substantially circular shapes shown in FIG. 9. It should be noted that it is preferable not to join continuously in the width direction in consideration of hindering the materials ability to stretch.

3. Components

The following explains the components in detail.

3-1. Top Sheet

The top sheet 2 can employ a liquid-permeable sheet to compose the entire top sheet 2 or a portion thereof. A resin film formed with a plurality of liquid-permeable holes in the same way as the liquid-permeable region composes all or a portion of the top sheet 2, with a net-shaped sheet having a plurality of networks, a liquid-permeable nonwoven fiber or fibers given as examples of the material that can be used in the top sheet 2. For example, polypropylene (PP), polyethylene (PE) or polyethylene terephthalate (PET) can be used to form the resin film or net-shaped sheet. A cellulose fiber such as rayon, a spun-laced nonwoven fiber formed of synthetic resin fibers, and through-air type nonwoven fiber formed using the synthetic resin fibers can be used as the nonwoven fibers. It is possible to use synthetic fibers of hydrophobic fiber and hydrophilic fiber as the fiber configuration of the through-air nonwoven fibers formed with air spaces between internal fibers.

It should be noted that in consideration of liquid penetration, it is preferred that density control is implemented that disposes higher density around the vicinity of a portion of the top sheet 2, an increasing gradient of densities in the top sheet 2 itself, or to apply differences in hydrophilicity to the top sheet 2.

3-2. Middle Sheet

The middle sheet 5 is disposed between the top sheet 2 and the absorbent body 4. It plays the roll of a support body for the absorbent body 4, and as a liquid-permeable sheet that gives the absorbent body 4 malleability and stability of form. A resin film formed with a plurality of liquid-permeable holes in the same way as the liquid-permeable region composes all or a portion of the middle sheet 5, which is a net-shaped sheet having a plurality of networks, with a liquid-permeable nonwoven fiber or fibers given as examples of the material that can be used in the middle sheet 5. For example, polypropylene (PP), polyethylene (PE) or polyethylene terephthalate (PET) can be used to form the resin film or net-shaped sheet. A cellulose fiber such as rayon, a spun-laced nonwoven fiber formed of synthetic resin fibers, and through-air type nonwoven fiber formed using the synthetic resin fibers can be used as the nonwoven fibers. It should be noted that in consideration of liquid penetration, it is preferred that density control is implemented that disposes higher density around the vicinity of a portion of the middle sheet 5, an increasing gradient of densities in the middle sheet 5 itself, or to apply differences hydrophilicity to the top sheet 2

3-3. Absorbent Body

As a material used in the absorbent body 4, softwood kraft pulp is ground and a highly absorbent polymer at a blend of 10% is added thereto, and enveloped by a tissue. However, the present invention is not limited to that. For example, it is also acceptable to use a material that blends thermally adhesive synthetic fibers to the ground pulp, or material that has been formed into a sheet shape using the airlaying technique or pulp, a spun-laced nonwoven fiber composed of cotton, rayon or pulp, or a mixture of these. It is also acceptable to use a material with elasticity, such as urethane or a cellulose sponge or the like. It should be noted that the present invention is in no way limited to the examples provided above or combinations thereof, and that the present invention can use any ordinary absorbent body.

3-4. Back Sheet

A material is used in the back sheet 3 that prevents excreta absorbed in the absorbent body 4 from leaking to the outside. By using a moisture-vapor permeable material, wearer discomfort and a sticky feeling when the sanitary napkin is worn are reduced. The back sheet 3 according the embodiments uses a liquid-impermeable polyethylene (PE) material, but this is not to be construed as a limitation to the present invention. For example, it is acceptable to use a sheet laminated with a resin film made by combining one or two types of the materials of polyethylene (PE), polypropylene (PP), polyethylene terephthalate (PET), and EVA resin, to add filler or the like to the resin film, and stretch it and form minute holes in the film to make it moisture-vapor permeable. Also possible are a laminated material of resin and paper, or a sheet laminated with nonwoven fibers and resin film. Preferably, a hydrophilic nonwoven fiber, an impermeable plastic film, or laminated sheet of nonwoven fibers and impermeable plastic film are used. In addition, it is acceptable to use an SMS nonwoven fiber that sandwiches a highly waterproof melt-blown nonwoven between a strong spun-bond nonwoven fiber.

3-5. Adhesive Body

The adhesive used in the slip-prevention adhesive portion 8 and adhesive portion 9 is a rubber-based hot-melt type, but this is not a limitation to the present invention. For example, an olefin type hot-melt, mechanical fasteners, or a styrene rubber based slip-prevention material can be used.

4. Manufacturing Apparatus

Figure 14:
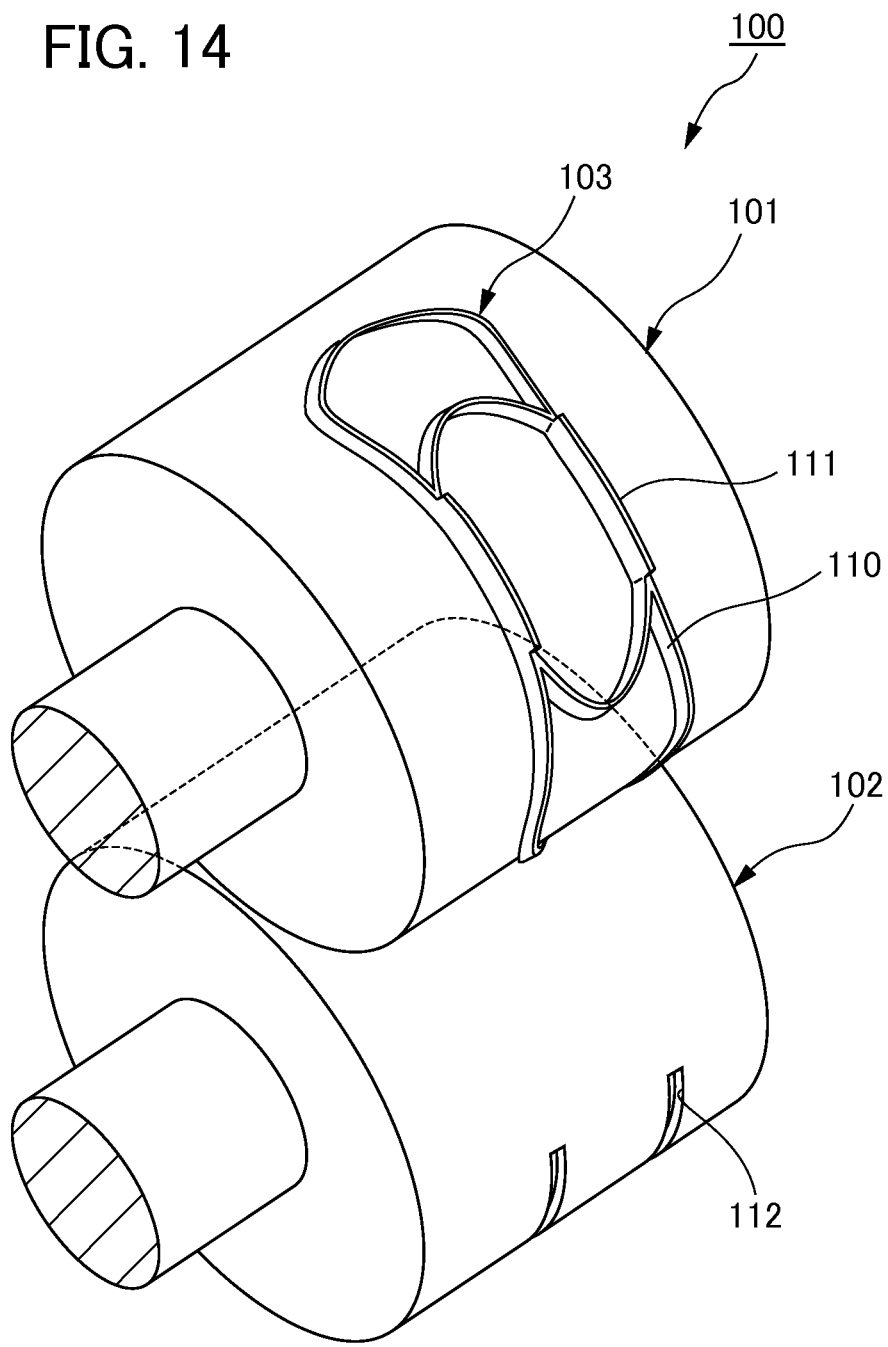
FIG. 14 is a view of an embossed roll.
Figure 15A:
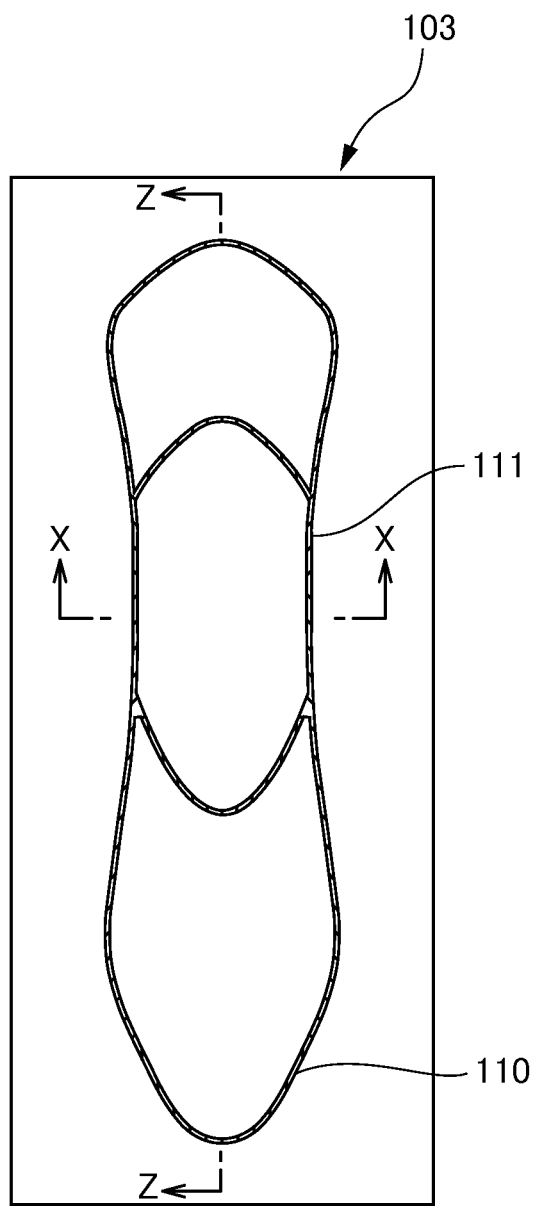
FIG. 15A is a view of an embossed pattern on a top embossed roll.
Figure 15B:
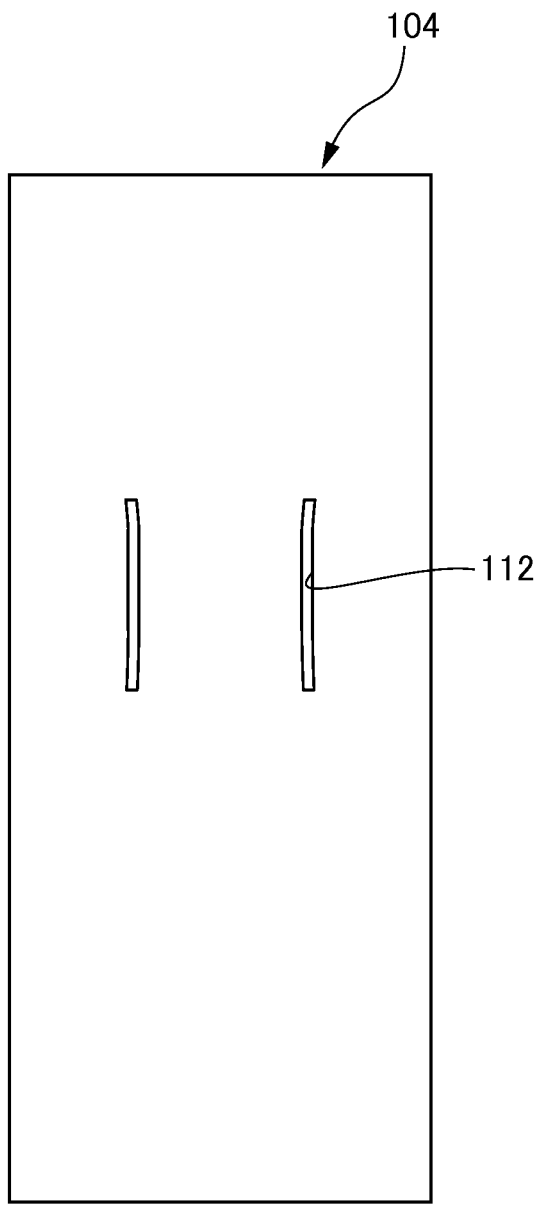
FIG. 15B is a view of an embossed pattern on a bottom embossed roll.
Figure 16:
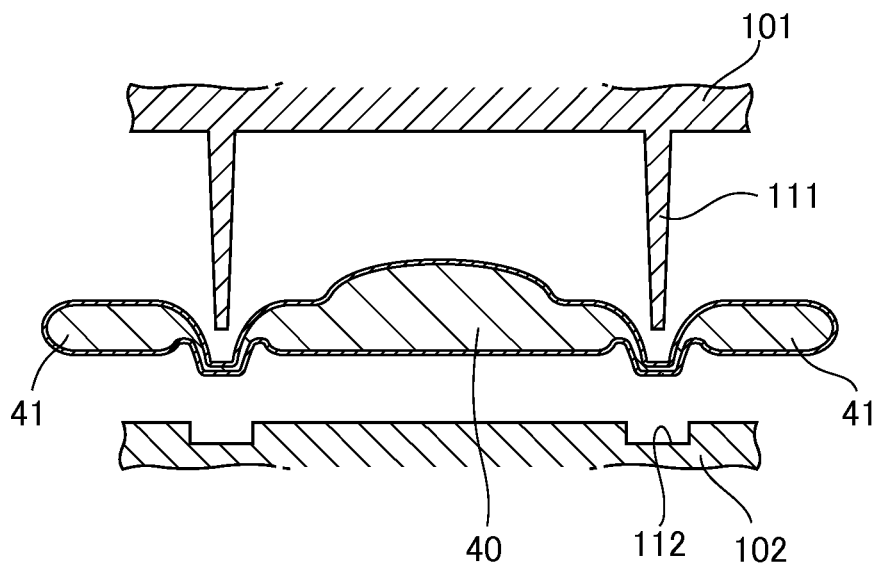
FIG. 16 is a view of an engagement of the embossed rolls of FIGS. 15A and 15B with the sanitary napkin.

The sanitary napkin 1 according to the present invention is formed using an embossing apparatus 100 provided with a pair of embossing rollers 101 and 102, as shown in FIGS. 14 to 16. As shown in FIG. 14, the embossing apparatus 100 is provided with an upper embossing roller 101 and a lower embossing roller 102. The upper and lower embossing rollers 101 and 102 each rotate a predetermined number of times. The sanitary napkin 1 is formed with the compressed channels 11 by passing between the upper embossing roller 101 and the lower embossing roller 102 while applying a predetermined amount of pressure and heat thereto.

It should be noted that as shown in FIG. 14, normally when considering the feeling of the sanitary napkin against the skin, the sanitary napkin is pressed by the male (convex) upper embossing roller 101 from the top sheet 2 side, and by the female (concave) lower embossing roller 102 from the back sheet 3 side to form the compressed channels 11. In addition, to form the compressed channels 11, it is preferred that the pressure bonding treatment be performed under heat and pressure.

As shown in FIG. 15A, the upper embossing roller 101 has the male (convex) upper embossing pattern 103 formed to a predetermined shape. As shown in FIG. 15B, the lower embossing roller 102 has the female (concave) lower embossing pattern 104 formed to a predetermined shape. As shown in FIG. 16, the compressed channels 11 according to the present invention are formed by each of the embossing patterns 101 and 102 being pressed into the sanitary napkin 1. Specifically, the compressed channels 11 are formed by the embossing teeth 111 of the upper embossing roller 101 and the female (concave) pattern 112 formed in the lower embossing roller 102 pressing together in the thickness direction (TD) with the embossing teeth 111 pressing into the female (concave) pattern from the surface side that contacts the wearer's skin, and the female (concave) pattern 112 pressing from the surface side that contacts the wearer's clothing.

Figure 17A:
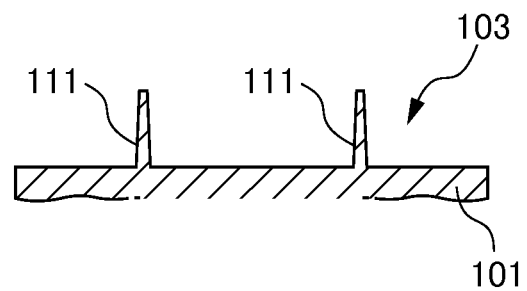
FIG. 17A is a sectional view of the embossed pattern through the line X-X shown in FIG. 15A.
Figure 17B:
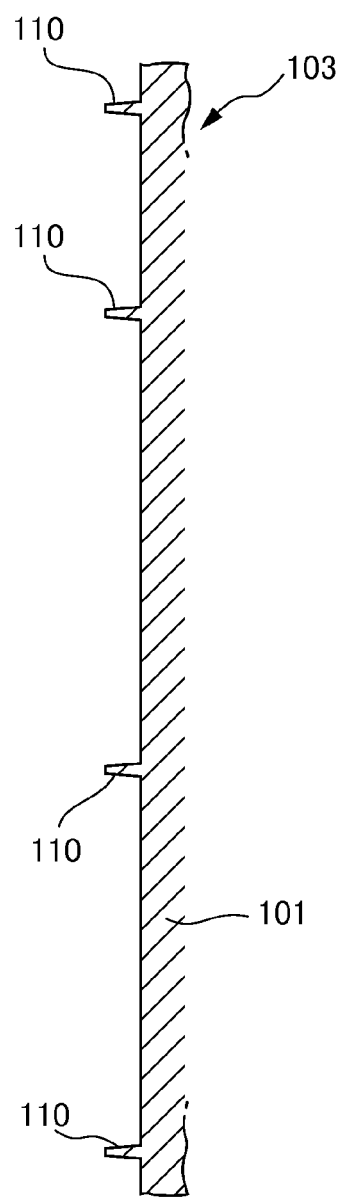
FIG. 17B is a sectional view of the embossed pattern through the line Z-Z shown in FIG. 15A.
Figure 17C:
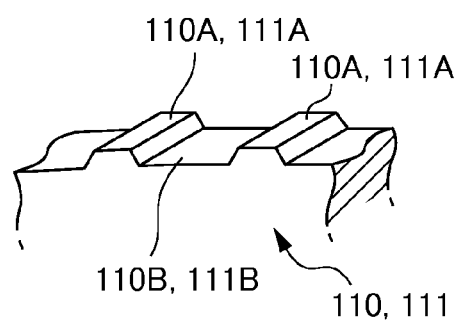
FIG. 17C is an enlarged view of embossed teeth of the embossed roll of FIG. 15A.

Specifically, as shown from FIGS. 17A to 17C, the embossing pattern 103 on the upper embossing roller 101 according to the first embodiment is provided with embossing teeth 110 and high embossing teeth 111. The high embossing teeth 111 are provided on both sides of the substantially oval-shape formed substantially in the center in the length direction (LD).

The high embossing teeth 111 and embossing teeth 110 are formed to an uneven shape where convex portions 111A (110A) and concave portions 111B (110B) are consecutively arranged, as shown in FIG. 17C. The concave portions 12 that are compressed to be high in the compressed channels 11 are formed by the convex portions 111A (110A), and the convex portions 13 that are compressed to be low are formed by the concave portions 111B (110B). It should be noted that according to the first embodiment, as the high embossing teeth 111 and the embossing teeth 110, an unevenly shaped portion where the convex portions 111A (110A) and the concave portions 111B (110B) are consecutively arranged, but this is not to be construed as a limitation to the present invention. It is also acceptable for this not to be uneven, but formed to a uniform height.

In addition, an embossing pattern 104 on the lower embossing roller 102 is formed to a female shape (concave shape) to enable the high embossing teeth 111 of the upper embossing roller 101 to mesh therein. Specifically, as shown in FIG. 18, projecting portions of the high embossing teeth 111 are formed to mate with the female (concave) portion of the engaging concave portion 112.

Figure 19:
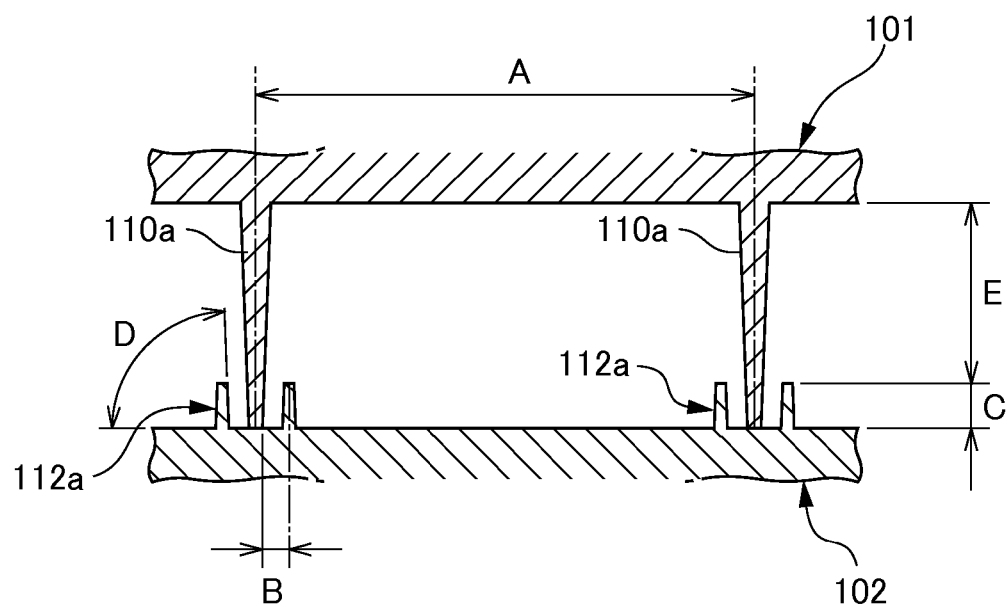
FIG. 19 is a sectional view of a state of engagement of a sanitary napkin embossing apparatus according to the second embodiment.

In addition, as shown in FIG. 19, embossing teeth 112a, substantially U-shaped in the profile, can be formed on the embossing pattern 104a of the lower embossing roller 102 by taking a shape that projects to the embossing teeth 110a on both sides of the engaging portion to enable engagement with the embossing teeth 110a of the upper embossing roller 101. It should be noted that the substantially U-shaped embossing teeth 112a are not uneven, but have a uniform height extending in series. However, the present invention is not limited to this shape and can use teeth where one or all have different heights. In other words, it is also acceptable to use shapes provided with consecutive concave and convex portions. In other words, the substantially U-shaped embossing teeth 112a can be intermittently projected and not consecutive. In this way, it is easier for the shapes of the projections 15 to be maintained in the compressed channels 11 by providing concave portions to part or all of the substantially U-shaped embossing teeth 112a.

Figure 18:
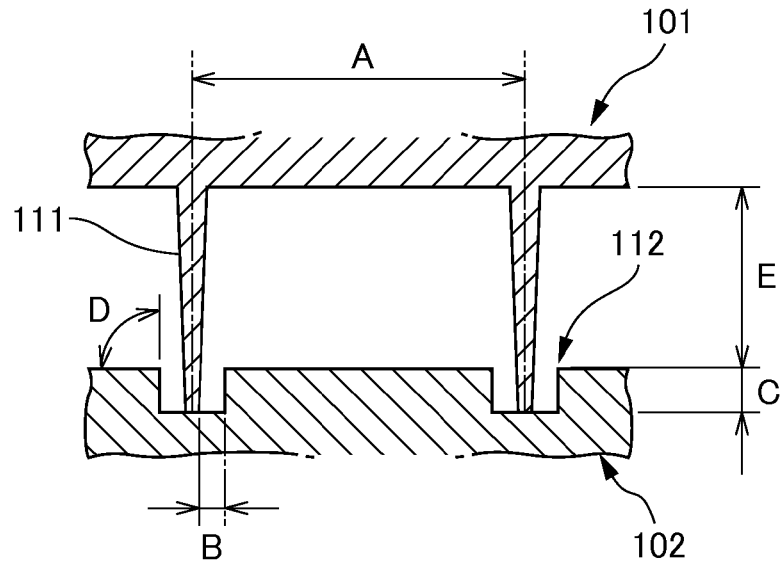
FIG. 18 is a sectional view of a state of engagement of a sanitary napkin embossing apparatus according to the first embodiment.

According to the first embodiment of the present invention, as shown in FIG. 18, embossing rollers 101 and 102 having the following dimensions may be used. For example, the convex portion pitch A of the upper embossing roller 101 may be 37 mm; the distance B of the engaging portion of the upper embossing roller 101 and the lower embossing roller 102 may be 0.75 mm; the engaging depth C for projecting the compressed channels 11 downward may be 3.0 mm; the side wall angle D that opposes the compressed channels 11 of the lower embossing roller 102 may be 90°; and the distance E from the bottom surface of the upper embossing roller 101 to the bottom surface of the lower embossing roller 102 may be 12 mm.

According to the second embodiment of the present invention, as shown in FIG. 19, embossing rollers 101 and 102 having the following dimensions may be used. For example, the convex portion pitch A of the upper embossing roller 101 may be 37 mm; the distance B of the engaging portion of the upper embossing roller 101 and the lower embossing roller 102 may be 0.75 mm; the engaging depth C for projecting the compressed channels 11 downward may be 3.0 mm; the side wall angle D that opposes the compressed channels 11 of the lower embossing roller 102 may be 80°; and the distance E from the bottom surface of the upper embossing roller 101 to the bottom surface of the lower embossing roller 102 may be 12 mm.

The convex portion pitch A of the upper embossing roller 101 is preferred to be in a range of 20 to 60 mm, or 30 to 50 mm because the core 40 deforms to a convex shape. If the convex portion pitch A is less than 25 mm, the distance from the compressed channels 11 to the center of the core 40 will be too short, which will require a large force to deform it to a convex shape, so deformation becomes difficult. If the convex portion pitch A is more than 50 mm, the distance of the compressed channels 11 will be too long, which will cause bending to occur in the compressed channels 11 while being deformed.

The distance B of the engaging portions of the upper embossing roller 101 and the lower embossing roller 102 is preferred to be in a range of 0.3 to 10 mm. More preferable is a range of 0.5 to 5.0 mm. In a case where the distance B of the engaging portions is less than 0.3 mm, these will not engage well when the basis weight of the absorbent body 4 is high. In a case where the distance B of the engaging portions is more than 10 mm, it may not be possible to form the compressed channels 11 to a projection when the basis weight of the absorbent body 4 is low.

The engaging depth C to project the compressed channels 11 downward is preferred to be in a range of 1 to 10 mm. More preferable is a range of 2 to 6 mm. If the engaging depth C is less than 1 mm, the engaging concave portions 112 may not be adequately formed and deformation will not be proper. In addition, if the engaging depth C is more than 10 mm, the absorbent body 4 of the engaging portions may be stretched too far to tear the absorbent body 4, and the compressed channels 11 and core 40 will be difficult to separate.

The range of the side wall angle D that opposes the compressed channels 11 of the lower embossing roller 102 is in the range of 30 to 120°. More preferable is the range of 45 to 100°. In a case where the side wall angle D is less than 30°, the forming of the projection of the compressed channels 11 toward the surface side that contacts the wearer's clothing will not be adequate. If the side wall angle D is more than 120°, the compressed channels 11 may get caught on the engaging portions after the engagement and they will not be easily pulled off from the metal plate (or metal roll), thereby hindering continuous production.

It is preferred that the distance E from the bottom surface of the upper embossing roller 101 to the bottom surface of the lower embossing roller 102 be in a range between 5 to 30 mm. More preferable is a range of 8 to 15 mm.

In this second embodiment, indentations are formed in the lower embossing roller 102 that correspond to the upper embossing roller 101; and convex portions are provided on the upper embossing roller 101 that engage the lower embossing roller 102, but the present invention is not limited to this configuration. The lower embossing roller 102 can be formed to a flat surface that does not have concavity or convexity, and be used with a manufacturing apparatus that uses a material that becomes concave when it is engaged with the upper embossing roller 101 and be able to realize the same format. For example, it is acceptable to use a material that changes in size when compressed, such as paper or a hard rubber.

Figure 20:
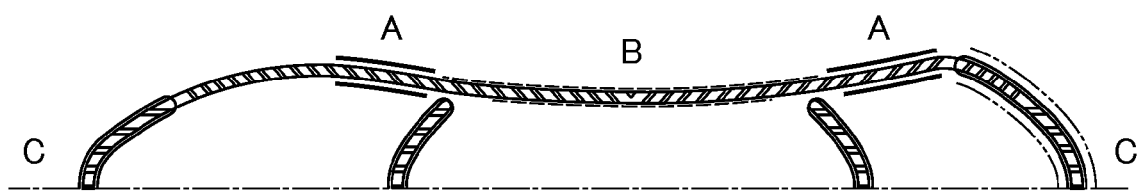
FIG. 20 is a view of encroachment positions of the embossed roll of FIG. 15A.

In addition, it is acceptable that the engaging concave portion 112 and embossing teeth 110 and 111 that form the compressed channels 11 be different according to the location to form the compressed channels 11. For example, FIG. 20 shows the positioning of the engaging concave portion 112 and embossing teeth 110 and 111. As shown in FIG. 20, the shapes used for the engaging concave portions 112 and embossing teeth 110 and 111 are different because of portions A, B, and C.

Figure 21A:
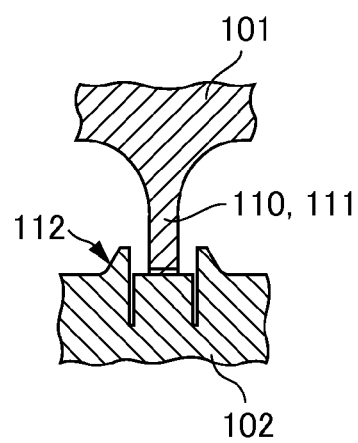
FIG. 21A is a sectional view illustrating the shape of the embossed teeth at a portion A of FIG. 20.
Figure 21B:
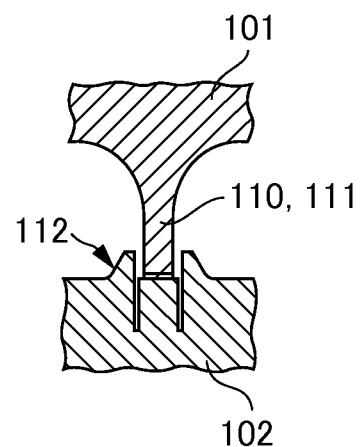
FIG. 21B is a sectional view illustrating the shape of the embossed teeth at a portion B of FIG. 20.

At the portion A, for example, the shapes of the engaging concave portions 112 and embossing teeth 110 and 111 shown in FIG. 21A are preferred. In addition, at the portion B, which is positioned near the area of excretion and differs from the portion A, the most pressure is received from the wearer's buttocks, so it is necessary to securely project that toward the surface side that contacts the wearer's clothing. Therefore, the engaging is stronger than the peripheral areas, and it is necessary to increase the stretching distance so that the shapes of the engaging concave portion 112 and embossing teeth 110 and 111 shown in FIG. 21B are preferred.

Figure 21C:
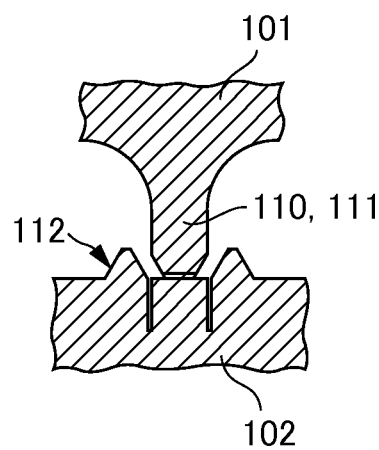
FIG. 21C is a sectional view illustrating the shape of the embossed teeth at a portion C of FIG. 20.

Moreover, since a projection is formed at the portion C that extends in the width direction (WD), it is easy for the absorbent body 4 to jam in the substantially U-shaped portion of the engaging portion of the embossing roller 102. Therefore, it is necessary to provide an incline to the side that contacts the embossing teeth 110 and 111 of the engaging concave portion 112 to make it easier to pull out the absorbent body 4 after the engagement. For example, the engaging concave portion 112 of the shapes shown in FIG. 21C are preferred. Since the embossing extends in the width direction (WD), the tearing of the sheet is facilitated by providing an angle to the embossing teeth 111 as shown in FIG. 21C.

5. Manufacturing Method

The manufacturing method of the sanitary napkin 1 according to the present invention is explained. The manufacturing method of the sanitary napkin 1 according to the present invention is configured with a compressed channel forming process that forms the compressed channels 11 that are concave to the surface side that contacts the wearer's skin, and spaces that project to the surface side that contacts the wearer's clothing by pressing the sanitary napkin 1 in the thickness direction (TD) from both the surface side that contacts the wearer's skin and the surface side that contacts the wearer's clothing. This compressed channel forming process has an upper die roller unit having a convex portion formed to a predetermined pattern on its surface, and a lower die roller unit having a concave portion formed to the predetermined pattern that can engage the convex portion. In addition, the sanitary napkin is formed by pressing an absorbent article material that includes at least an absorbent body in the thickness direction (TD).

The sanitary napkin 1 according to the present invention is formed with compressed channels 11 and spaces 16, the sanitary napkin 1 being passed between the upper die roller and the lower die roller while applying a predetermined pressure and heat thereto. When the sanitary napkin passes through, the absorbent article that includes at least the absorbent body is compressed in the thickness direction (TD). This compressing can be consecutive or compressed at predetermined intervals. It should be noted that this manufacturing method is omitted because it supports the description of the manufacturing apparatus.

Targets for manufacturing by this manufacturing method are a substantially longitudinally shaped sanitary napkin 1 having at least a portion of a liquid-permeable top sheet 2 having a width direction (WD) and a length direction (LD) that is perpendicular to the width direction (WD), and is disposed on a surface side that contacts the wearer's skin; a liquid-impermeable back sheet 3 disposed on a surface side that contacts the wearer's clothing; and an absorbent body disposed between the top sheet 2 and the back sheet 3. In addition, compressed channels are formed on the surface side of the absorbent body that contacts the wearer's skin. The compressed channels separate the core disposed with the absorbent body at a center area of the width direction, and the side portions disposed on both sides of the core in the width direction. The sanitary napkin forms the surfaces that contact the wearer's clothing in the compressed channels to project to the surface side that contacts the wearer's clothing more than the surfaces on the core that contact the wearer's clothing in the thickness direction (TD) of the absorbent article.

It is within the scope of the present invention to include all foreseeable equivalents to the elements of the present invention as described with reference to FIGS. 1-21C. The examples provided are not to be interpreted as limiting the invention beyond that which is claimed.

What is claimed is:

1. An absorbent article comprising:
   a top sheet having at least a portion thereof being liquid-permeable and disposed on a body-facing side;
   a liquid-impermeable back sheet disposed on a clothing-facing side; and
   a liquid-retainable absorbent body disposed between the top sheet and the back sheet, a portion of the back sheet defining a planar back face portion of the absorbent article, wherein
   the absorbent body comprises:
   an absorbent core enveloped in a tissue, the tissue comprising a folded portion at the body-facing side of the absorbent core along a length direction of the absorbent article, and the folded portion being configured to extend when the absorbent core is deformed;
   a compressed channel portion formed to be a concave shape in the body-facing side toward the clothing-facing side; and
   at least one space having a convex shape formed in the clothing-facing side toward the body-facing side; wherein
   the at least one space is further formed in at least one side of a channel backside of the compressed channel portion in the clothing-facing side, and
   the channel backside projects toward the clothing-facing side more than the planar back face portion of the absorbent article.

2. The absorbent article according to claim 1, wherein the absorbent core is in substantially a center of the absorbent body; and
   the space is formed in at least a core side of the opposing sides of channel backside.

3. The absorbent article according to claim 1, wherein at least a portion of the top sheet is formed to enable stretching in a width direction that is perpendicular to a length direction of the absorbent article.

4. The absorbent article according to claim 1, wherein at least a portion of the body-facing side in the absorbent body is formed to enable stretching in a width direction of the absorbent article.

5. The absorbent article according to claim 1, wherein at least a portion of the channel backside is bonded to the back sheet.

6. The absorbent article according to claim 1, wherein adhesive portions are disposed on the clothing-facing back sheet at a side of the channel backside.

7. The absorbent article according to claim 1, wherein the absorbent body is configured to be pushed upward by the channel backside fitting into the spaces.

8. The absorbent article according to claim 1, wherein the top sheet has a higher ability to stretch in a width direction of the absorbent article than the absorbent body.

* * * * *